US011357925B2

(12) United States Patent
Dugand et al.

(10) Patent No.: US 11,357,925 B2
(45) Date of Patent: Jun. 14, 2022

(54) AUTOMATIC INJECTION DEVICE PROVIDED WITH A DEVICE FOR GENERATING SOUND SIGNALS

(71) Applicant: Nemera La Verpillière, La Verpilliere (FR)

(72) Inventors: Pascal Dugand, Estrablin (FR); Kevin Stamp, Sheffield (GB)

(73) Assignee: Nemera La Verpillière

( * ) Notice: Subject to any disclaimer, the term of this patent is extended or adjusted under 35 U.S.C. 154(b) by 139 days.

(21) Appl. No.: 16/609,075

(22) PCT Filed: Apr. 10, 2018

(86) PCT No.: PCT/FR2018/050892
§ 371 (c)(1),
(2) Date: Oct. 28, 2019

(87) PCT Pub. No.: WO2018/197774
PCT Pub. Date: Nov. 1, 2018

(65) Prior Publication Data
US 2020/0147311 A1  May 14, 2020

(30) Foreign Application Priority Data

Apr. 28, 2017 (FR) ...................................... 1753772

(51) Int. Cl.
*A61M 5/315* (2006.01)
*A61M 5/20* (2006.01)
*A61M 5/32* (2006.01)

(52) U.S. Cl.
CPC ........ *A61M 5/3157* (2013.01); *A61M 5/2033* (2013.01); *A61M 5/3202* (2013.01);
(Continued)

(58) Field of Classification Search
CPC ............ A61M 2205/43; A61M 5/3157; A61M 2205/581; A61M 5/20
See application file for complete search history.

(56) References Cited

U.S. PATENT DOCUMENTS

| 8,734,402 | B2 * | 5/2014 | Sharp | ..................... A61M 5/002 604/223 |
| 2011/0092915 | A1 * | 4/2011 | Olson | ................. A61M 5/3202 604/198 |

(Continued)

FOREIGN PATENT DOCUMENTS

| WO | 2014166892 A1 | 10/2014 |
| WO | 2016001304 A1 | 1/2016 |
| WO | WO-2016075254 A1 * | 5/2016 | .......... A61M 5/3234 |

*Primary Examiner* — Nilay J Shah
*Assistant Examiner* — Robert F Allen
(74) *Attorney, Agent, or Firm* — St. Onge Steward Johnston & Reens LLC

(57) ABSTRACT

An automatic injection device includes an injection syringe for injecting liquid provided with a syringe body carrying an injection needle and a piston rod mounted to be able to move inside this syringe body to cover an injection stroke during which the liquid is injected, an external casing and a positioning control member that are telescopic, the relative movement of which controls the operation of the automatic injection device, and control members arranged to selectively control the movement of the syringe body and the movement of the piston inside the positioning control member in order to automatically inject the liquid present in the injection syringe, the automatic injection device further comprising a device for generating sound signals activated during the automatic injection of the liquid present in the injection syringe so as to generate a series of sound signals from the start to the end of the injection.

9 Claims, 5 Drawing Sheets

(52) U.S. Cl.
 CPC ... *A61M 2205/43* (2013.01); *A61M 2205/581* (2013.01); *A61M 2205/583* (2013.01)

(56) References Cited

U.S. PATENT DOCUMENTS

2012/0172811 A1* 7/2012 Enggaard ............... A61M 5/20
 604/193
2016/0361503 A1* 12/2016 Bendek ................... A61M 5/46

* cited by examiner

AUTOMATIC INJECTION DEVICE PROVIDED WITH A DEVICE FOR GENERATING SOUND SIGNALS

FIELD OF THE INVENTION

This invention relates to the field of automatic injection devices for liquids, especially pharmaceutical.

BACKGROUND OF THE INVENTION

Such automatic injection devices are used in particular in the medical field, for automatic administration of a liquid medication requiring an injection. Such a device allows in particular a person, for example suffering from rheumatoid arthritis, multiple sclerosis, diabetes or undergoing an anaphylactic shock in case of allergy, to inject themselves a dose of medication independently.

An automatic injection device comprising a syringe for injecting liquid provided with a syringe body carrying an injection needle and a piston rod mounted so as to be able to move inside this syringe body in order to cover an injection stroke during which the liquid is injected has already been proposed, especially in document U.S. Pat. No. 8,734,402. The automatic injection device comprises an external casing and a positioning control member that are telescopic, the relative movement of which controls the operation of this automatic injection device. In addition, control members are arranged to selectively control the movement of the syringe body and the movement of the piston inside the positioning control member in order to automatically inject the liquid present in the syringe.

This automatic injection device advantageously ensures that the injection dosing does not depend on the force applied on the external casing but only on the positioning control member and the control members, which avoids incorrect dosing.

However, since injection is automatic, it is not easy for the user to know when all the liquid medicine has been administered.

SUMMARY OF THE INVENTION

The invention aims to remedy these disadvantages by providing an automatic injection device which indicates when to remove the automatic injection device from the skin of the person into whom the liquid is injected.

The invention therefore concerns an automatic injection device comprising an injection syringe for injecting liquid provided with a syringe body carrying an injection needle and a piston rod mounted so as to be able to move inside this syringe body in order to cover an injection stroke during which the liquid is injected, an external casing and a positioning control member that are telescopic, the relative movement of which controls the operation of the automatic injection device, and control members arranged to selectively control the movement of the syringe body and the movement of the piston inside the positioning control member in order to automatically inject the liquid present in the syringe, characterized in that the automatic injection device further comprises a device for generating sound signals activated during the automatic injection of the liquid present in the syringe.

Advantageously according to the invention, the automatic injection device generates a series of sound signals from the start to the end of the injection to indicate when to remove the automatic injection device from the skin of the person into whom the liquid is injected. In fact, when the user hears no more sound signals, he/she deduces that the injection is finished and that the automatic injection device can be removed from the skin of the person into whom the liquid was injected.

According to other optional characteristics of the invention:
- the device for generating sound signals is mounted between the positioning control member and one of the control members to generate sound signals during the relative movement between the syringe body and the piston;
- the device for generating sound signals is mounted between the positioning control member and the syringe body control member;
- the device for generating sound signals is mounted between the positioning control member and the piston control member;
- the device for generating sound signals comprises at least one elastic hook-toothing assembly for generating a sound signal each time the elastic hook crosses a tooth of the toothing;
- the device for generating sound signals comprises two elastic hook-toothing assemblies;
- the two elastic hook-toothing assemblies are offset to generate two alternating sound signals;
- each toothing is arranged on the positioning control member;
- the automatic injection device further comprises an element providing a visual indication of the injection stroke;
- the visual indication element comprises at least one visual indicator positioned next to a window formed on the external casing at the end of the injection stroke.

BRIEF DESCRIPTION OF THE DRAWINGS

Other features and advantages will appear clearly on reading the description which follows, given by way of example and not limiting in any way, referring to the attached drawings, in which.

DETAILED DESCRIPTION OF THE INVENTION

On the various figures, elements which are similar or identical have the same reference numbers, possibly with an index added. Their structures and functions are therefore not systematically described.

Figure 1:
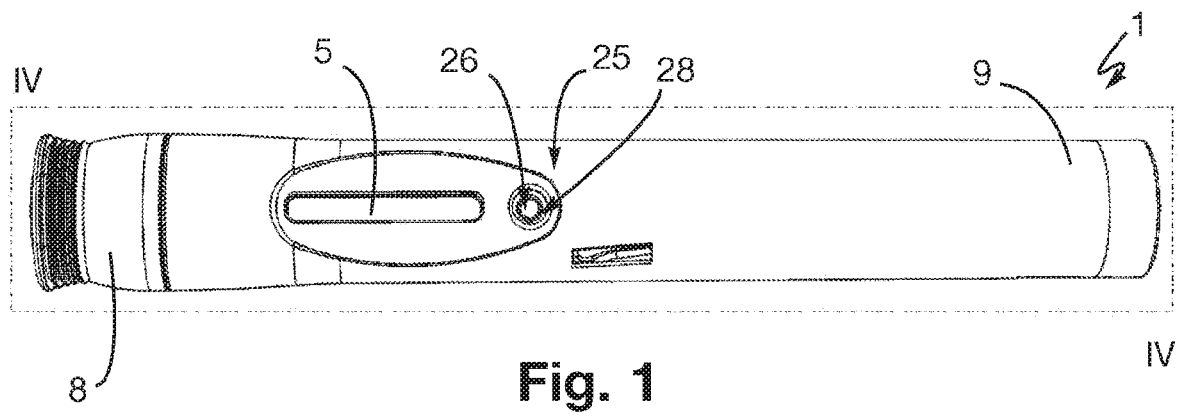
FIG. 1 is a perspective view of an automatic injection device according to the invention.
Figure 2:
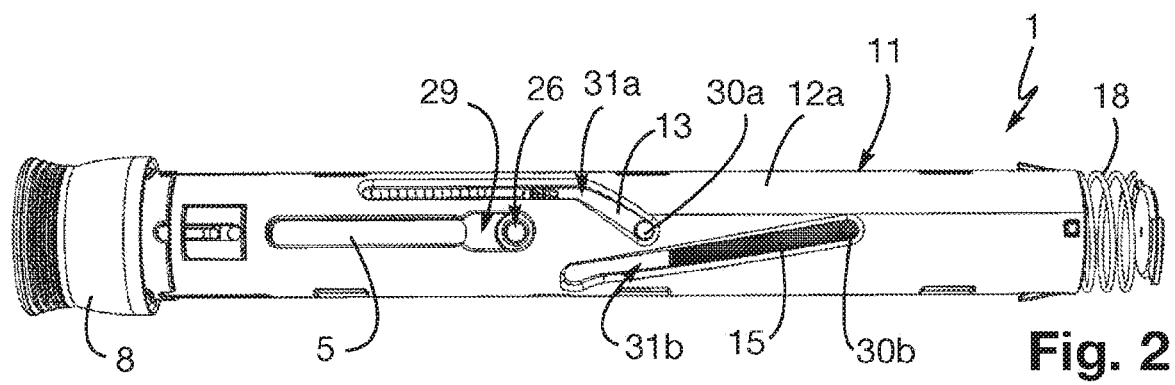
FIG. 2 is a perspective view of the automatic injection device of FIG. 1, with the external casing hidden.
Figure 3:
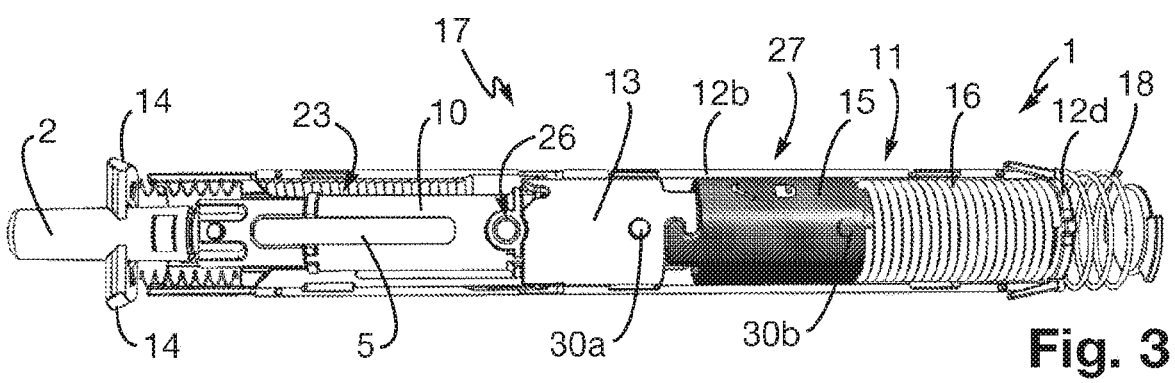
FIG. 3 is a perspective view of the automatic injection device of FIG. 1, with the external casing, a portion of the positioning control member and the protective cap hidden.
Figure 4:
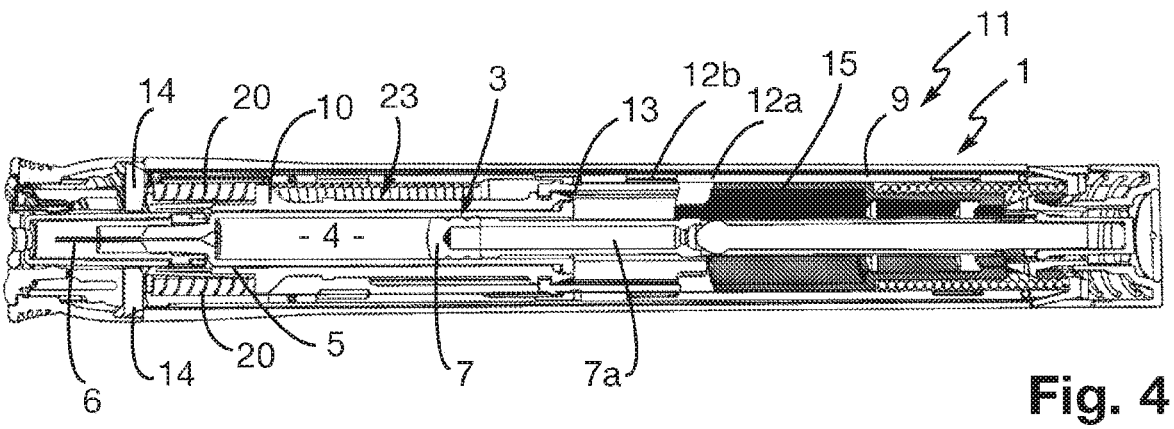
FIG. 4 is a cross-sectional view of the automatic injection device along the plane IV-IV of FIG. 1.
Figure 5:
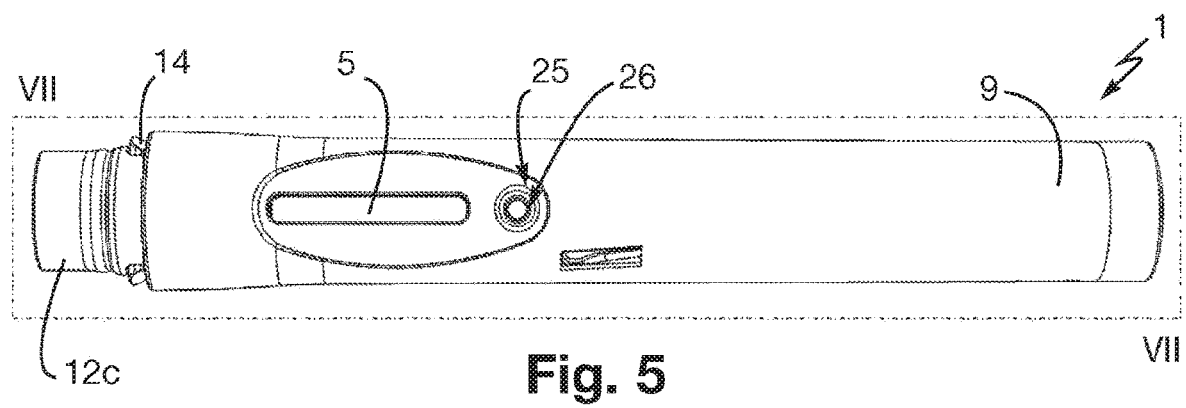
FIG. 5 is a perspective view of the automatic injection device of FIG. 1 after removing the protective cap.
Figure 6:
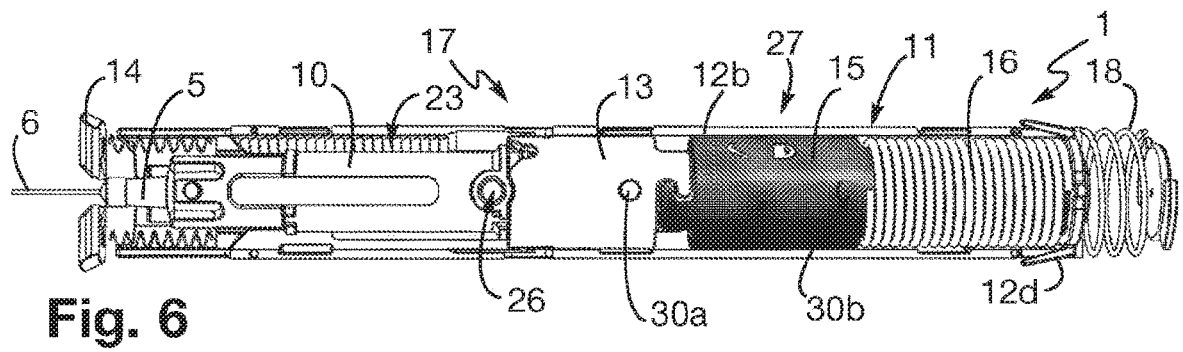
FIG. 6 is a perspective view of the automatic injection device of FIG. 5, with the external casing and a portion of the positioning control member hidden.
Figure 7:
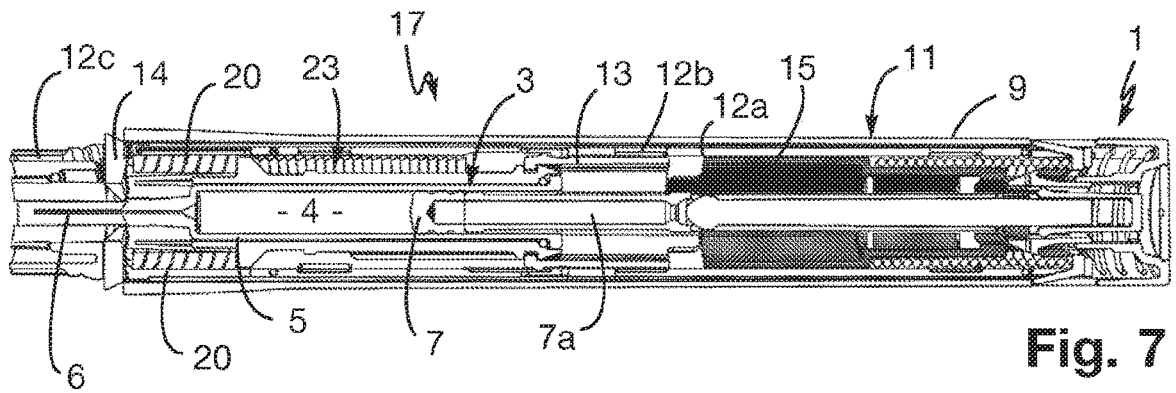
FIG. 7 is a cross-sectional view of the automatic injection device along the plane VII-VII of FIG. 5.

In the remainder of the document, the orientations are given relative to the user. In particular, the terms "distal" and "proximal" are generally understood to be relative to the distance from the hand of the user holding the automatic injection device. More precisely, referring to FIG. 1, the user applies his/her hand on the proximal end of the automatic injection device, on the right on FIG. 1.

As shown on FIGS. 1 to 4, the invention concerns an automatic injection device 1 intended to preferably receive an injection syringe 3. The injection syringe 3 may be for example a prefilled glass cemented needle syringe, of volume 1 milliliter. However, the injection syringe 3 could be replaced, for example, by a cartridge provided with an injection needle.

The automatic injection device 1 may thus comprise an injection syringe 3 containing a liquid 4, for example, of the pharmaceutical type as explained in the technical background of the invention. The injection syringe 3 is preferably provided with a syringe body 5 carrying an injection needle 6 and a piston 7 rod 7a mounted so as to be able to move inside this syringe body 5 in order to cover an injection stroke during which the liquid 4 is injected by the automatic injection device 1.

More precisely, the automatic injection device 1 comprises an external casing 9 forming a gripping element for a user and a positioning control member 11, the external casing 9 and the positioning control member 11 being telescopic so that their relative movement controls the operation of the automatic injection device 1 as explained below.

In addition, the automatic injection device 1 comprises control members 13, 15 arranged to selectively control the movement of the syringe body 5 and the movement of the piston 7 inside the positioning control member 11 in order to automatically inject the liquid 4 present in the injection syringe 3.

Advantageously, the automatic injection device 1 according to the invention further comprises a device 17 for generating sound signals intended to indicate when to remove the automatic injection device 1 from the skin of the person into whom the liquid 4 is injected. Advantageously, the device 17 for generating sound signals is activated during the automatic injection of the liquid 4 present in the injection syringe 3 so as to generate a series of sound signals continuously substantially between the start and the end of the injection.

Thus, when the user no longer hears sound signals, he/she deduces that the injection is finished and that the automatic injection device 1 can be removed from the skin of the person into whom the liquid 4 was injected, the user being said person or not.

In order to generate sound signals during the relative movement between the syringe body 5 and the piston 7, the device 17 for generating sound signals is preferably mounted between the positioning control member 11 and one of the control members 13, 15. As explained below, in fact, once the syringe body 5 control member 13 is disengaged, the liquid 4 will be injected with a joint movement of the syringe body 5 control member 13 and of the piston 7 control member 15 relative to the positioning control member 11. We therefore understand that the device 17 for generating sound signals can be mounted either between the positioning control member 11 and one of the two control members 13, 15 or both of them.

The device 17 for generating sound signals comprises at least one assembly 19 of the elastic hook 21-toothing 23 type. Each assembly 19 is preferably intended to generate a sound signal each time the elastic hook 21 crosses a tooth 24 of the toothing 23. We therefore understand that each toothing 23 of an assembly can be mounted either on the positioning control member 11 or on one of the two control members 13, 15 or both of them and, inversely, for each elastic hook 21.

Obviously, depending on the required implementations, each assembly 19 may comprise one (or more) toothing(s) 23 interacting with one (or more) elastic hook(s) 21. For example, an assembly 19 could thus comprise a single elastic hook 21 mounted on the positioning control member 11 interacting consecutively, depending on the progress of the injection, with a first toothing 23 mounted on the syringe body 5 control member 13 and a second toothing 23 mounted on the piston 7 control member 15.

Figure 8:
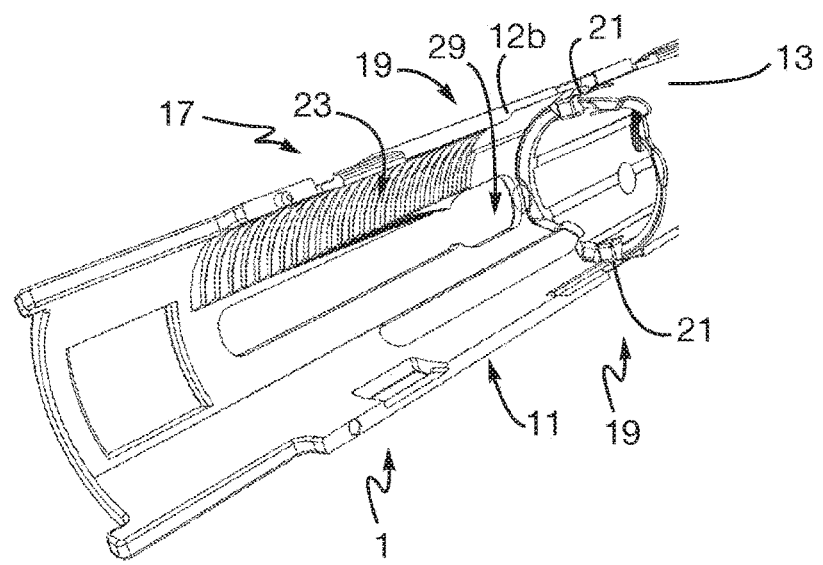
FIG. 8 is a perspective view of the automatic injection device of FIG. 5 showing the positioning of a portion of the device for generating sound signals according to the invention.

As shown in particular on FIG. 8 and in a non-limiting way, the following explanation will be given for a device 17 for generating sound signals comprising two assemblies 19 each with an elastic hook 21 mounted on the syringe body 5 control member 13 and a toothing 23 mounted on the positioning control member 11. More precisely, the syringe body 5 control member 13 thus comprises two elastic hooks 21 mounted symmetrically at one of its ends so that each one interacts with a toothing 23 mounted on one of the shells 12a, 12b of the positioning control member 11.

Advantageously, according to the invention, several assemblies 19 can be used to generate sound signals that are louder or even detectable by touch by gripping the external casing 9. This also allows each assembly 19 to be offset in order to generate two alternating sound signals. We therefore understand that, for a given injection stroke and a given number of sound signals, the distance between the teeth 24 of each toothing 23 can be twice as long, therefore making the toothings 23 easier to manufacture.

In addition, the automatic injection device 1 may also comprise an element 25 providing a visual indication of the injection stroke. Such a visual indication element 25 may thus comprise at least one visual indicator 26, 27, such as a pictogram, carried by one of the control members 13, 15 or by the positioning control member 11. At the end of the injection stroke, a visual indicator of the end of the injection stroke 27 can therefore be positioned next to windows 28, 29 formed respectively on the external casing 9 and, optionally, the positioning control member 11, to be visible by the user.

The automatic injection device 1 is in a configuration shown on FIGS. 1 to 4, which will be referred to as a configuration before use in which the element 25 providing a visual indication of the injection stroke shows the ready-for-use visual indicator 26. This ready-for-use visual indicator 26 is carried by the syringe support 10 and can be seen since it is positioned opposite the windows 28 and 29 formed respectively on the external casing 9 and the positioning control member 11 to show that the automatic injection device 1 is ready for use.

To operate the automatic injection device 1, the protective cap 8 must first be removed from the distal part of the automatic injection device 1 in order to remove the syringe stopper 2 surrounding the injection needle 6.

The automatic injection device 1 is in a configuration shown on FIGS. 5 to 8, which will be referred to as the initial configuration. The user then grasps the automatic injection device 1 by the external casing 9 and presses the distal surface of the end sleeve 12c against the skin at the position where the liquid 4 contained in the syringe body 5 is to be injected. As shown on FIG. 8, we see that the syringe body 5 control member 13 is in a position in which the elastic hooks 21 are angularly offset relative to the toothings 23. In addition, the syringe body 5 control member 13 is positioned upstream from the windows 29 of the shells 12a, 12b of the positioning control member 11. We therefore understand that the element 25 providing a visual indication of the injection stroke still shows the ready-for-use visual indicator 26.

Then, during an unlocking step, the user applies an axial force, towards the distal part of the automatic injection device 1, on the external casing 9. Thus, the external casing 9 moves, telescopically, axially towards the distal part of the positioning control member 11. This movement releases the ring 12d retaining the positioning control member 11 which, incidentally, no longer immobilizes the piston 7 control member 15 with the positioning control member 11. The unlocking step may be accompanied by a sound signal generated by the release of the control member 15 relative to the retaining ring 12d. The automatic injection device 1 therefore reaches the configuration in which the piston 7 control member 15 is free to move axially towards the distal part of the positioning control member 11.

During this step, the two locking elements 14, mounted sliding substantially radially in two slots provided in the end sleeve 12c, slide substantially radially so as to be in a configuration allowing immobilization of the injection syringe 3, in which the locking elements 14 are brought together so that the space between the locking elements 14 is small enough to retain the injection syringe 3 axially by its distal shoulder.

Figure 9:
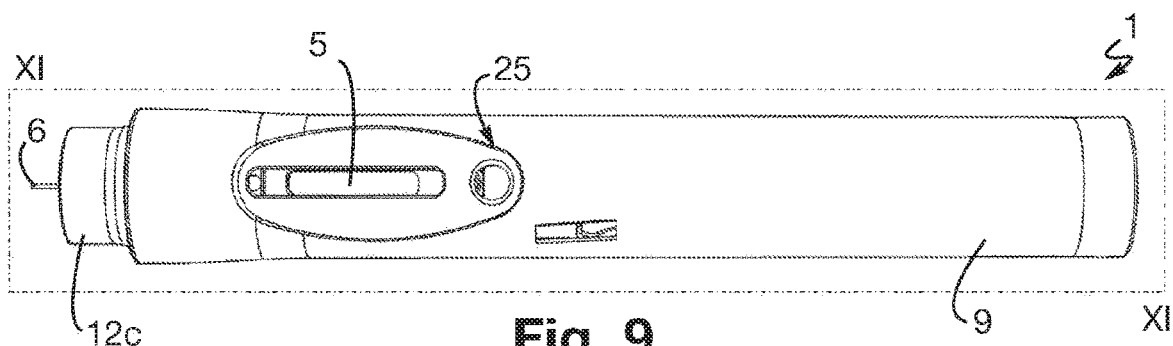
FIG. 9 is a perspective view of the automatic injection device of FIG. 1 after inserting the needle into the patient's skin.
Figure 10:
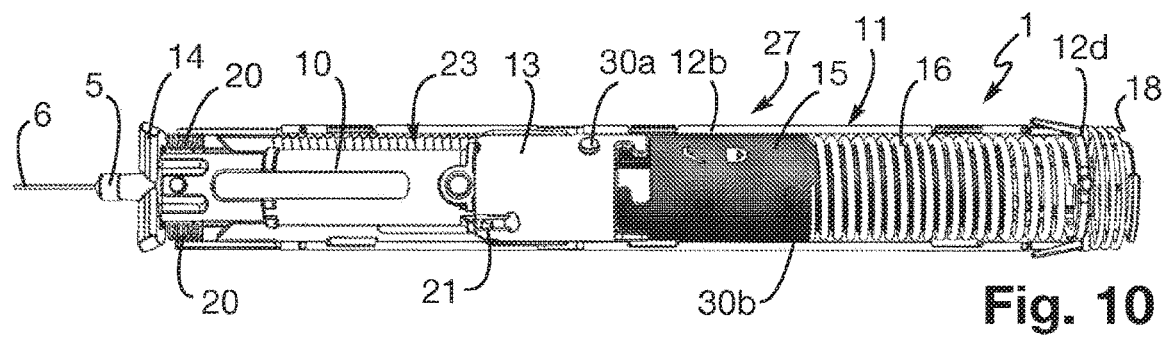
FIG. 10 is a perspective view of the automatic injection device of FIG. 9, with the external casing and a portion of the positioning control member hidden.
Figure 11:
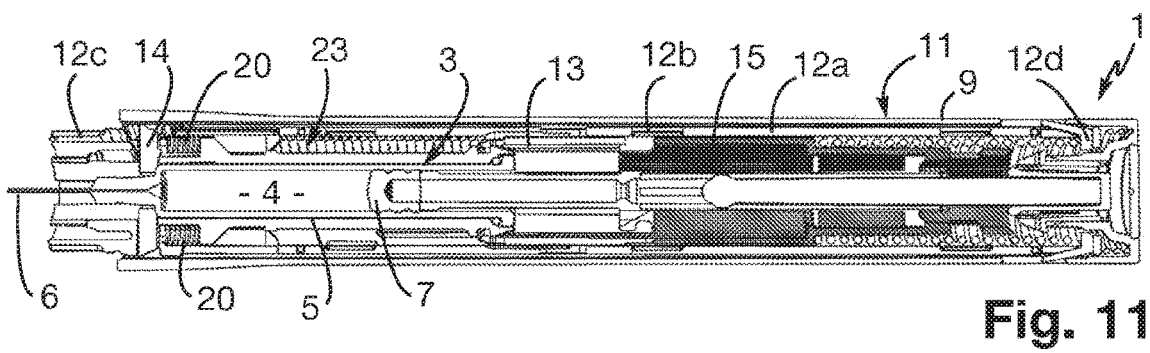
FIG. 11 is a cross-sectional view of the automatic injection device along the plane XI-XI of FIG. 9.
Figure 12:
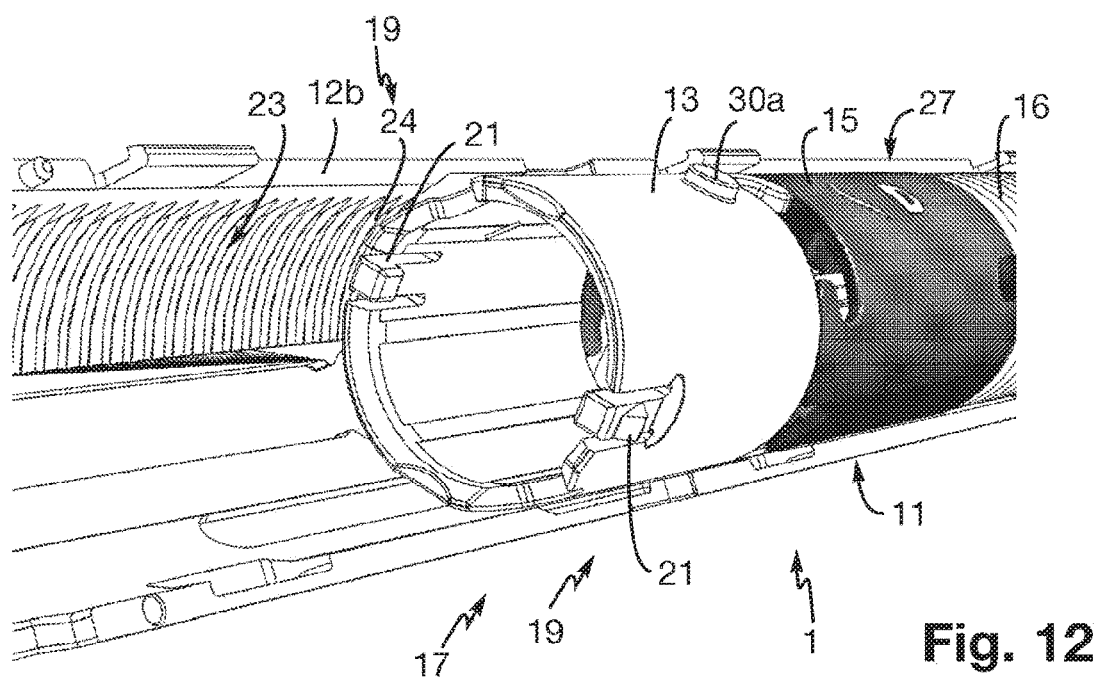
FIG. 12 is a perspective view of the automatic injection device of FIG. 9 showing the positioning of a portion of a device for generating sound signals according to the invention.
Figure 13:
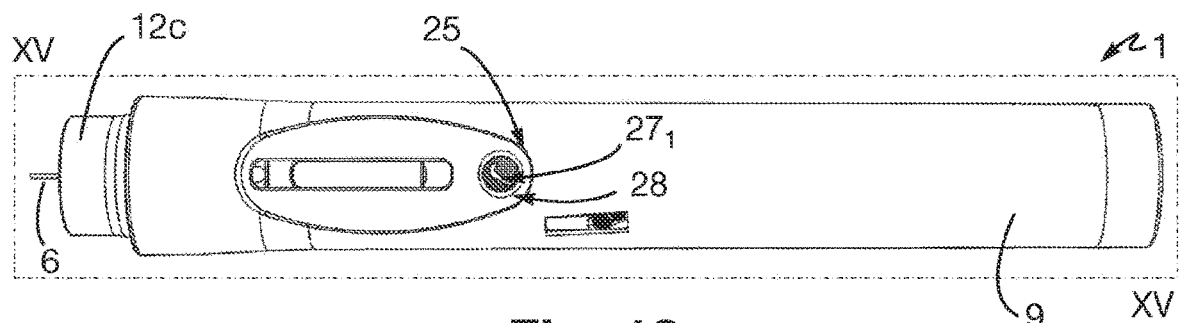
FIG. 13 is a perspective view of the automatic injection device of FIG. 1 after injecting liquid into the patient's skin.
Figure 14:
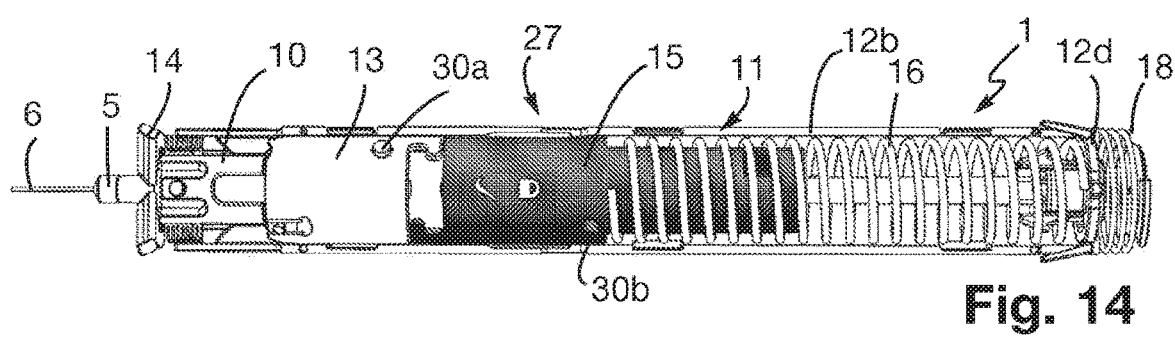
FIG. 14 is a perspective view of the automatic injection device of FIG. 13, with the external casing and a portion of the positioning control member hidden.
Figure 15:
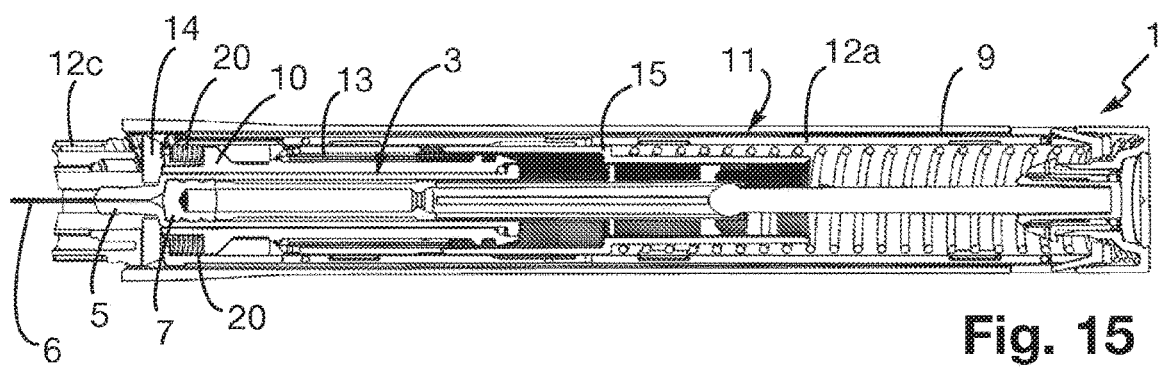
FIG. 15 is a cross-sectional view of the automatic injection device along the plane XV-XV of FIG. 13.
Figure 16:
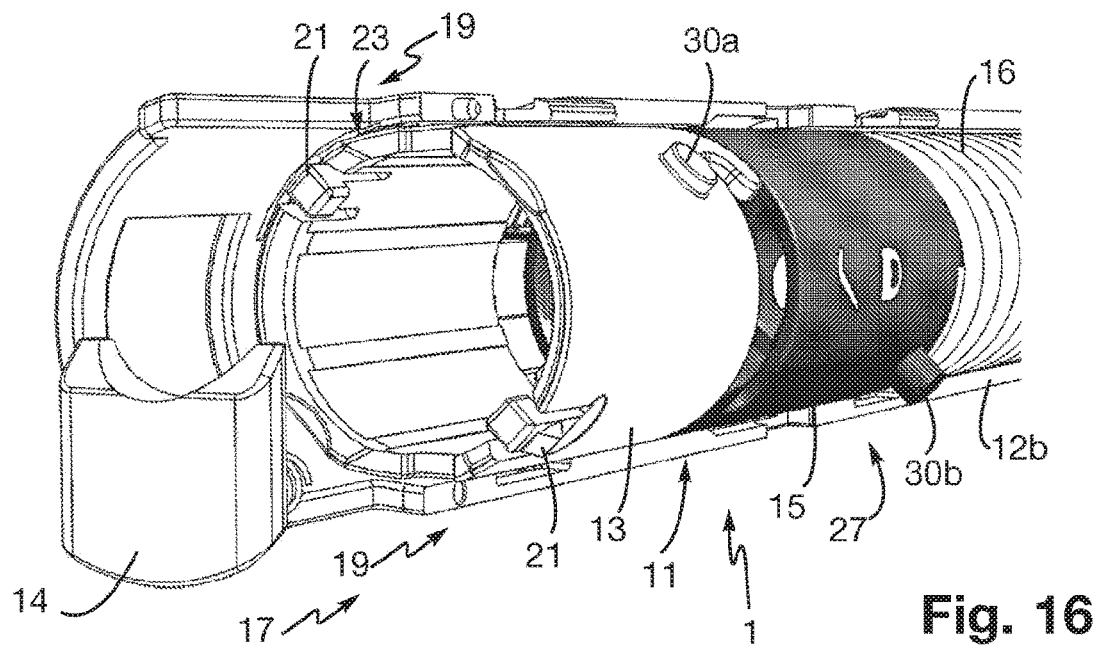
FIG. 16 is a perspective view of the automatic injection device of FIG. 13 showing the positioning of a portion of a device for generating sound signals according to the invention.

An insertion step occurs after this unlocking step. The injection spring 16 pushes axially the syringe body 5 and piston 7 control members 13, 15 towards the distal part of the positioning control member 11. Since the syringe body 5 control member 13 is in the configuration in which it is engaged with the syringe support 10, it interacts axially with the syringe support 10 and moves the latter so that the injection needle 6 now projects relative to the distal surface of the end sleeve 12c as shown on FIG. 9 and is inserted into the patient's skin. Advantageously, as shown on FIGS. 10 and 11, since the locking elements 14 are in their immobilization configuration, the injection syringe 3 is held axially when the injection needle 6 is inserted into the patient's skin to limit its penetration.

During this step, the cam 30a of the syringe body 5 control member 13 interacts with a first camway 31a of the positioning control member 11 so that the syringe body 5 control member 13 turns relative to the syringe support 10 up to its configuration in which it is disengaged from the syringe support 10. Similarly, the cam 30b of the piston 7 control member 15 interacts with a second camway 31b of the positioning control member 11 so that the piston 7 control member 15 turns relative to the piston 7 rod 7a. However, the piston 7 control member 15 does not reach its configuration in which it is disengaged from the piston 7 rod 7a. At the end of this step, the automatic injection device 1 is in the configuration shown on FIGS. 9 to 12, in which the piston 7 control member 15 is in its configuration engaged with the piston 7 rod 7a and the syringe body 5 control member 13 is in its disengaged configuration.

In this configuration, the injection needle 6 is inserted into the patient's skin. The element 25 providing a visual indication of the injection stroke virtually no longer shows the ready-for-use visual indicator 26 and shows the outer surface of the syringe body 5 control member 13. We therefore understand that the syringe body 5 control member 13 may comprise a particular color and/or a graduation used to indicate the progress of the injection. As shown on FIG. 12 in fact, we see that the syringe body 5 control member 13 is in a position in which the elastic hooks 21 are now aligned with the toothings 23 and whose outer surface is positioned in front of the windows 29 of the shells 12a, 12b of the positioning control member 11 and of the windows 28 of the external casing 9. However, the elastic hooks 21 have not started to interact with the toothings 23.

An injection step occurs after this insertion step. The injection spring 16 continues to push axially the syringe body 5 and piston 7 control members 13, 15 towards the distal part of the positioning control member 11, however, the syringe body 5 control member 13 no longer interacts axially with the syringe support 10. Since the piston 7 control member 15 is in the configuration in which it is engaged with the piston 7 rod 7a, it pushes the latter so that it covers its injection stroke. The liquid 4, for example pharmaceutical, is then injected into the patient's body.

The element 25 providing a visual indication of the injection stroke then shows consecutively the outer surface of the syringe body 5 control member 13 then the outer surface of the piston 7 control member 15. In addition, since the device 17 for generating sound signals is advantageously activated, the elastic hooks 21, now aligned with the toothings 23, interact with their respective teeth 24 so as to generate a series of sound signals continuously substantially between the start and the end of the automatic injection of the liquid 4 present in the injection syringe 3.

During this step, the cam 30b of the piston 7 control member 15 continues to interact with the second camway 31b, by relative movement, but does not reach its configuration in which it is disengaged from the piston 7 rod 7a. At the end of this step, the automatic injection device 1 is in the configuration shown on FIGS. 13 to 16, in which the piston 7 and the piston 7 rod 7a abut against the bottom wall of the syringe body 5 and the piston 7 control member 15 is in the configuration in which it is engaged with the piston 7 rod 7a.

The element 25 providing a visual indication of the injection stroke now shows the pictogram $27_1$ of the end of injection stroke 27 visual indicator present on the outer surface of the piston 7 control member 15 indicating that the injection is finished. We see in fact that the pictogram $27_1$ of the piston 7 control member 15 is positioned in front of the windows 29 of the shells 12a, 12b of the positioning control member 11 and the windows 28 of the external casing 9. In addition, as shown on FIG. 16, the syringe body 5 control member 13 is in a position in which the elastic hooks 21 have reached the end of the toothings 23 and can therefore no longer generate sound signals.

Advantageously according to the invention, the arrangement of the device 17 for generating sound signals therefore offers a longitudinal movement which generates a unique sound pattern changing throughout the injection stroke. As a comparison in fact, a circumferential movement requires the use of a sound pattern which has to be repeated to cover the entire injection, thereby generating uncertainty regarding the progression of the injection. Consequently, the longitudinal movement can, advantageously according to the invention, create a unique changing and customizable pattern depending on the sound signals required.

A retraction triggering step occurs after this injection step. Since the user no longer hears sound signals and can see the pictogram $27_1$, he/she deduces that the injection is finished. The user therefore releases the axial force applied on the external casing 9 so that the return spring 18 can move the external casing 9 in the direction of telescopic elongation of the automatic injection device 1. This action by the user therefore triggers retraction of the injection needle 6. During this movement, the first camway 31a interacts with the cam 30a of the piston 7 control member 15 which drives in rotation the piston 7 control member 15 relative to the piston 7 rod 7a up to its disengaged configuration. At the end of this step, the automatic injection device 1 is in the configuration in which the piston 7 control member 15 is in its configuration in which it is disengaged from the piston 7 rod 7a, and the radial projections of the retaining ring 12d interact with the edges of the holes formed in the external casing 9.

A retraction step occurs after this retraction triggering step. Since the piston 7 control member 15 is in the configuration in which it is disengaged from the piston 7 rod 7a, the latter is free to move axially towards the proximal part of the automatic injection device 1. The retraction springs 20 are then free to push the syringe support 10 towards the proximal part of the positioning control member 11. Thus, the injection needle 6 retracts into the positioning control member 11 so that it no longer projects past the distal surface of the end sleeve 12c. Advantageously, the retraction is accompanied by a sound signal which can be generated by the movement of the control member 15 relative to the head of the piston 7 rod 7a.

Figure 17:
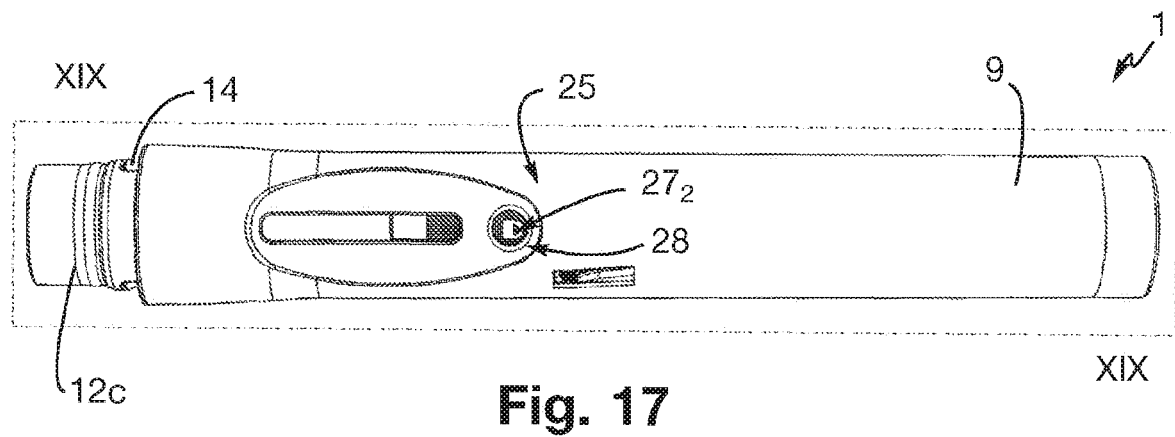
FIG. 17 is a perspective view of the automatic injection device of FIG. 1 after retracting the needle.
Figure 18:
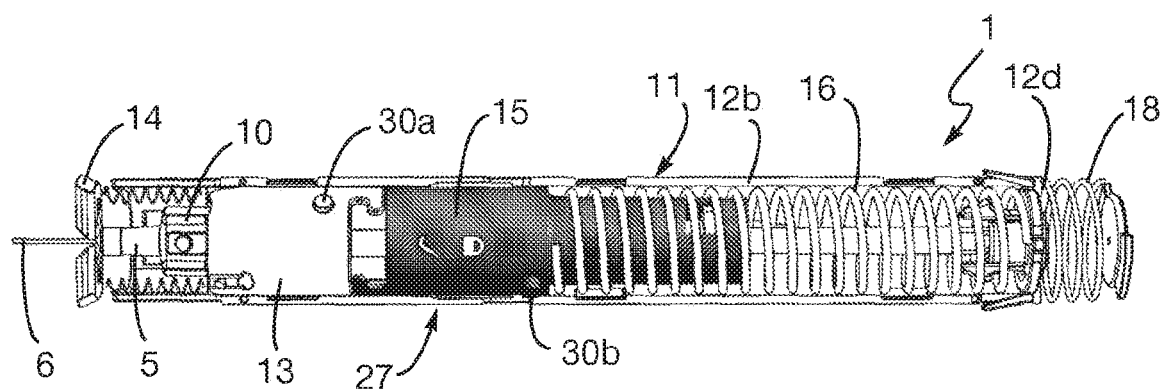
FIG. 18 is a perspective view of the automatic injection device of FIG. 17, with the external casing and a portion of the positioning control member hidden.
Figure 19:
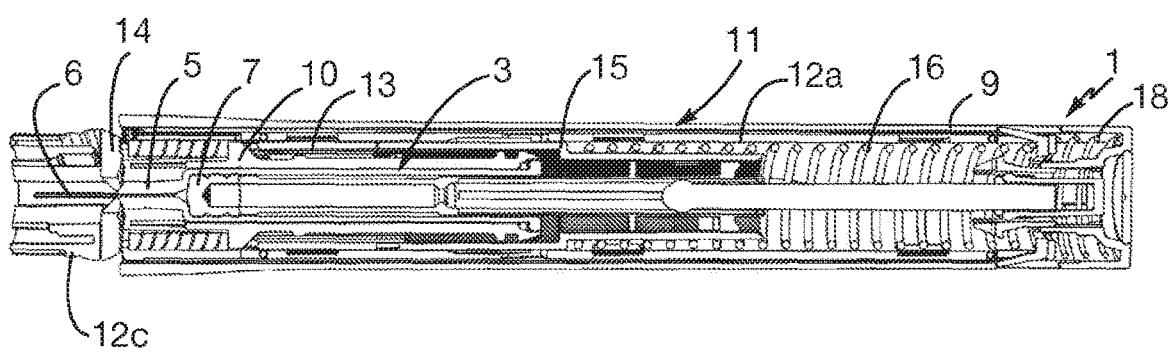
FIG. 19 is a cross-sectional view of the automatic injection device along the plane XIX-XIX of FIG. 17.

At the end of this step, the automatic injection device 1 is in the configuration shown on FIGS. 17 to 19, in which the operation of the automatic injection device 1 is finished. The element 25 providing a visual indication of the injection stroke then shows the pictogram $27_2$ of the end of injection stroke 27 visual indicator present on the outer surface of the piston 7 control member 15 indicating that the automatic injection device 1 has already been used. We see in fact that the pictogram $27_2$ of the piston 7 control member 15 is positioned in front of the windows 29 of the shells 12a, 12b of the positioning control member 11 and of the windows 28 of the external casing 9.

The invention is not limited to the embodiment described and the variants proposed and other embodiments and variants will be clearly apparent to those skilled in the art. In particular, the device 17 for generating sound signals could be active before the start of injection such as, for example, from the time the user presses the external housing 9 in order to generate sound signals before the start of the injection.

Thus, each assembly 19 of the device 17 for generating sound signals can be adapted according to the required implementations so as to adjust the start, the intensity, the frequency and the end of the sound signals. For example, a first toothing 23 could thus interact with a first elastic hook 21 throughout the duration of the automatic injection device 1 while a second toothing 23 could interact with a second elastic hook 21 only during the injection step so as to vary the intensity and/or frequency of the sound signals during the duration of the injection step compared with the rest of the operating steps of the automatic injection device 1. As an additional example, the distance between the teeth of either one of the toothings can be variable so that, for example, the frequency of the sound signals increases or decreases at the end of injection. Similarly, the height of the teeth of either one of the toothings can be variable so that, for example, the sound level of the sound signals increases or decreases according to the progress of the injection.

In addition, each visual indication element 25 can be adapted according to the required implementations to adjust the start, information, and end of the displays shown.

According to an embodiment not shown, the invention could provide for a toothing whose spacing between the teeth could vary from one area of the toothing to another. This spacing may vary regularly or not. Thus, an initial portion of toothing could have an initial spacing and a final portion of toothing (at end of injection) could have a final spacing less than the initial spacing. Optionally, one or more portions of intermediate toothings, each provided with a spacing between teeth that is intermediate between the initial and final spacings, could be planned between the initial and final portions of toothing. A spacing changing progressively, for example decreasing such that the frequency of the sound signal is higher at the end of the injection than at the start, could also be planned.

The invention claimed is:

1. An automatic injection device comprising:
an injection syringe for injecting a liquid provided with a syringe body carrying an injection needle and a piston rod mounted so as to move inside the syringe body in order to cover an injection stroke during which the liquid is injected,
an external casing,
a positioning control member, wherein the external casing and the positioning control member are telescopic, and wherein a relative movement of the external casing and the positioning control member controls an operation of the automatic injection device, and
a first control member and a second control member, wherein the first control member is configured to control a movement of the syringe body and wherein the second control member is configured to control a movement of the piston rod inside the positioning control member in order to automatically inject the liquid present in the injection syringe,
wherein the automatic injection device further comprises a device for generating sound signals activated during an automatic injection of the liquid present in the injection syringe so as to generate a series of sound signals from a start to an end of the injection, and wherein the device for generating sound signals is mounted between the positioning control member and the first control member or the second control member to generate sound signals during a relative movement between the syringe body and the piston rod.

2. The automatic injection device according to claim 1, wherein the device for generating sound signals is mounted between the positioning control member and the first control member configured to control the movement of the syringe body.

3. The automatic injection device according to claim 1, wherein the device for generating sound signals is mounted between the positioning control member and the second control member configured to control the movement of the piston rod.

4. The automatic injection device according to claim 1, wherein the device for generating sound signals comprises at least one elastic hook-toothing assembly for generating a sound signal each time the elastic hook crosses a tooth of the toothing.

5. The automatic injection device according to claim 4, wherein the at least one elastic hook-toothing assembly comprises two elastic hook-toothing assemblies.

6. The automatic injection device according to claim 5, wherein the two elastic hook-toothing assemblies are offset to generate two alternating sound signals.

7. The automatic injection device according to claim 5, wherein each toothing is arranged on the positioning control member.

8. The automatic injection device according to claim 1, further comprising an element providing a visual indication of the injection stroke.

9. The automatic injection device according to claim 8, wherein the visual indication element comprises at least one visual indicator positioned next to a window formed on the external casing at an end of the injection stroke.

* * * * *